Figure 1:
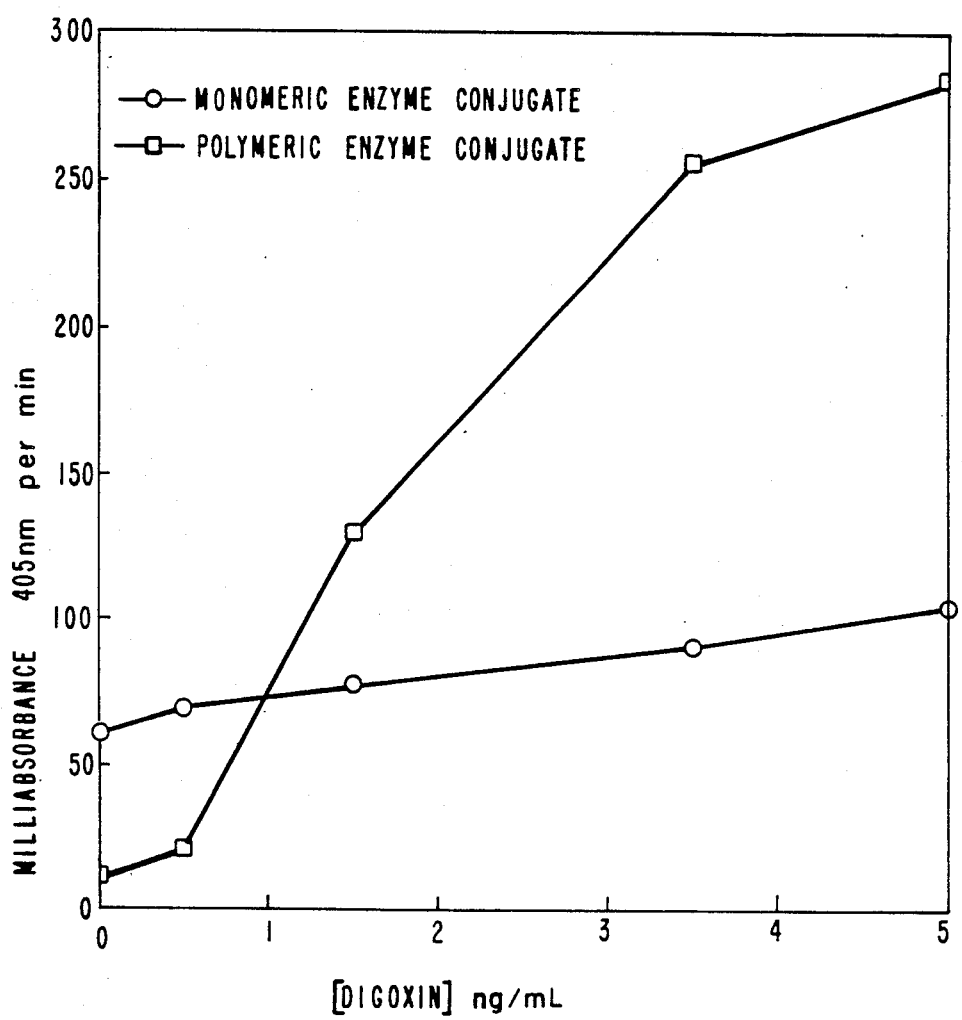

United States Patent [19]

Freytag et al.

[11] Patent Number: 4,657,853
[45] Date of Patent: Apr. 14, 1987

[54] IMMUNOASSAYS UTILIZING COVALENT CONJUGATES OF POLYMERIZED ENZYME AND ANTIBODY

[75] Inventors: J. William Freytag, Wilmington, Del.; Eiji Ishikawa, Miyazaki, Japan

[73] Assignee: E. I. Du Pont de Nemours and Company, Wilmington, Del.

[21] Appl. No.: 650,868

[22] Filed: Sep. 14, 1984

[51] Int. Cl.[4] .................. G01N 33/50; G01N 33/563; C12Q 1/00; C12N 9/96

[52] U.S. Cl. ............................................ 435/7; 435/4; 435/188; 435/810; 436/512; 436/547

[58] Field of Search ........................ 435/7, 188, 810, 4; 436/512, 538, 547

[56] References Cited

U.S. PATENT DOCUMENTS 3,654,090 4/1972 Schuurs et al. ........................ 435/7
4,200,436 4/1980 Mochida et al. ..................... 436/512
4,410,634 10/1984 Cooper et al. ....................... 436/500

OTHER PUBLICATIONS

Avrameas et al., C. R. Academy Science Paris, Ser. D 262, (1966) pp. 2543–2545 (Translation).
Leary et al., 1983, P.N.A.S., 80:4045–4049.
Butler et al., 1981, Methods in Enzymology, 73:482–523.
Holbeck et al., 1983, J. Immunol. Methods, 60:47–52.
Ishikawa et al., 1983, Immunoenzymatic Techniques, Avreamas et al. (Eds.), Elseiver Science Publ. B.V. pp. 219–232.
Imagawa et al., 1982, J. Appl. Biochem., 4:400–410.
Boorsma et al., 1979, J. Immunol. Methods 30:245–255.
Nakane et al., 1966, J. Histochem. Cytochem., 14:929.
Engvall et al., 1971, Immunochemistry, 8:871.
Freytag et al., 1984, Clin. Chem., 84:417–420.
Guesdon et al., 1983, J. Immunol. Methods, 58:133–142.
Yolken et al., 1983, J. Immunol. Methods, 56:319–327.

*Primary Examiner*—Sidney Marantz
*Assistant Examiner*—Patricia Kate White

[57] ABSTRACT

An enzyme is cross linked to form a polymerized enzyme which is covalently coupled to an antibody or antibody fragment. The use of the antibody-polymeric enzyme conjugate in immunoassays provides enhanced signal generation and, therefore, short assay time and high sensitivity.

22 Claims, 2 Drawing Figures 4,657,853

IMMUNOASSAYS UTILIZING COVALENT CONJUGATES OF POLYMERIZED ENZYME AND ANTIBODY

BACKGROUND

The first use of enzyme-labeled antibodies in immunocytochemical detection was reported in 1966 by Avrameas and Uriel [C. R. Seances Acad. Sci. Ser., D262, 2543 (1966)] and Nakane and Pierce [J. Histochem. Cytochem., Volume 14:929 (1966)]. The importance of these enzyme-labeled antibodies in diagnostic medicine was not understood accurately until about 1971, when Engvall and Perlmann [Immunochemistry, Volume. 8, 871 (1971)] and van Weeman and Schuurs [U.S. Pat. No. 3,654,090 (1972)] described the use of antibody-enzyme conjugates in quantitative enzyme-linked immunoassays. Since that time, there have been numerous publications describing procedures for coupling antibodies and their fragments to various enzymes.

A class of heterogeneous immunoassay which is achieving widespread use and which employs an enzyme-labeled antibody is referred to as an immunometric assay. One type of immunometric assay is the so-called sandwich assay. In a sandwich assay, a ternary complex is formed from (i) a solid-phase, unlabeled antibody, (ii) the analyte of interest, and (iii) a soluble, labeled antibody. Sandwich assays require the compound of interest to be polyvalent, i.e. to have two or more different antigenic determinants or a single, multiply occurring determinant.

Sandwich assays can be divided into forward, reverse, and simultaneous assays, depending on the method of addition of the labeled antibody. In a forward sandwich assay, the labeled antibody is added to a preformed binary complex of solid-phase antibody and analyte. In a reverse sandwich assay, labeled antibody and analyte are allowed to complex before addition of the solid-phase antibody. In a simultaneous sandwich, the sample containing analyte is contacted simultaneously with both the labeled and the solid-phase antibodies. Forward assays require two washing steps, while reverse and simultaneous assays require only a single washing step.

A single antibody immunometric assay, first described by Schuurs and van Weeman [U.S. Pat. No. 3,654,090 (1972)] and extended by Mochida and Ogawa [U.S. Pat. No. 4,200,436 (1980)] and Freytag et al. [Clinical Chem., Volume 84, 417 (1984)] adds elements of simplicity, speed, versatility, and overall sensitivity. Furthermore, the analyte need not be polyvalent. In this assay format, an excess of labeled antibody (preferably monovalent) is mixed with a sample containing analyte. After a brief incubation period to allow binding of the analyte, excess unreacted labeled antibody is removed by exposure of the mixture to antigen which has been immobilized on a solid support. The free (or bound) fraction is then quantified and is a direct measure of the analyte concentration.

It has been shown that the quality and nature of the antibody-enzyme conjugate has profound influence on the ultimate usefulness of an immunoassay for the quantitation of antigens. Ishikawa et al. report that monomeric non-aggregated Fab'/enzyme conjugates yield the lowest non-specific background and the highest sensitivity, particularly in sandwich-type double antibody immunometric assays [Immunoenzymatic Techniques, ed. S. Avrameas, Elsevier Science Publ. B.V. pp. 219-232 (1983)]. Monomeric Fab-enzyme conjugates are also necessary for maximum performance in single antibody immunometric assays [Ishikawa, cited above, and co-pending patent application (IP-0458)]. However, when very low levels of analyte are being analyzed (<1 fmole), these assays require extended incubation periods for the generation of significant quantities of enzymic product for measurement.

Covalent methods for coupling single enzyme molecules to single coupling sites on antibodies are known, e.g. Imagawa et al., J. Appl. Biochem, Volume 4, 400 (1982).

It has been appreciated for some time now that aggregated antibody-enzyme conjugates can provide enhanced signal generation over that of purely monomeric antibody-enzyme conjugates. Aggregated antibody-enzyme conjugates generally have been prepared using nonspecific coupling chemistries such as glutaraldehyde crosslinking [Engvall & Perlmann, Immunochemistry, Volume 8, 871 (1971)] or periodate oxidation [Boorsma & Streefkerk, J. Immunol. Methods, Volume 30, 245 (1979)]. The preparation of these conjugates involves a random crosslinking process in which the antibody or antibody-fragments can be buried deep within an aggregated complex, thus remaining largely inaccessible for antigen binding. In addition, these amorphous macromolecular complexes are difficult to prepare in a reproducible fashion. Immunoassays utilizing such aggregated antibody-enzyme conjugates routinely suffer from very high background blanks due to nonspecific binding, and the ultimate sensitivity achievable in immunometric assays is dramatically reduced [Ishikawa et al., Ann. Clin. Biochem., Volume 19, 379 (1982)].

Leary et al. report the formation of polymerized alkaline phosphatase by crosslinking the monomeric enzyme with disuccinimidyl suberate. The polymeric enzyme was then biotinylated with biotinyl-ε-aminocaproic acid N-hydroxysuccinimide ester. The biotinylated enzyme was then reacted with an excess of avidin. The resulting conjugate was then reacted with biotinylated nucleic acid probes leading to a noncovalent linkage of polymerized enzyme to probe. [Leary et al., P.N.A.S. (U.S.A.), Volume 80, 4045 (1983).]

A number of procedures have been reported that utilize noncovalent chemistry to generate antibody-enzyme conjugates with high enzyme-to-antibody ratios. For example, Butler describes an antibody-enzyme conjugate comprising immune complexes of peroxidase-antiperoxidase antibody or phosphatase-antiphosphatase antibody. [Butler, Methods Enzymol., Volume 73:482-523 (1981)]. Halbeck and Nepom describe an antibody-enzyme conjugate comprising complexes of protein A and anti-protein A-horseradish peroxidase conjugates. [Holbeck & Nepom, J. Immunol. Methods, Volume, 60, 47 (1983)]. Guesdon et al. describe a procedure for preparing antibody-enzyme complexes using conjugates of bovine serum albumin and enzyme labeled anti-bovine serum albumin antibody. [Guesdon et al., J. Immunol. Methods, Volume 58, 133 (1983)]. Finally, Yolken et al., describe antibody-enzyme conjugates comprising complexes of avidin and enzyme-labeled biotin. [Yolken et al., J. Immunol. Methods, Volume 56, 319 (1983)]. The aforementioned procedures all suffer from the disadvantage that the linkage of antibody to enzyme is not covalent, and, therefore, a reversible binding results which is susceptible of unwanted dissociation.

There is a need for a highly reproducible procedure for the preparation of convalently linked polymeric-enzyme/antibody conjugates in which both original enzymatic activity as well as original immunoreactivity are maintained.

DISCLOSURE OF INVENTION

This need is met by the present invention which, in one aspect, is a process for producing a polymeric-enzyme/antibody conjugate, comprising the sequential steps of:

(a) covalently coupling at least two enzyme molecules to produce a prepolymerized enzyme; and (b) coupling covalently the prepolymerized enzyme to an antibody or fragment thereof.

In another aspect, the invention is an immunoassay utilizing covalent conjugates of prepolymerized enzyme and antibody or antibody fragments.

In another aspect, the invention is a covalent conjugate of an antibody and a prepolymerized enzyme.

DESCRIPTION OF INVENTION

In general, the process of this invention should apply to virtually any enzyme that can be coupled to an antibody for use in an immunoassay. Suitable enzymes are β-D-galactosidase,
glucose oxidase,
horseradish peroxidase,
alkaline phosphatase,
β-lactamase,
glucose-6-phosphate dehydrogenase,
urease,
uricase,
superoxide dismutase,
luciferase,
pyruvate kinase,
lactate dehydrogenase,
galactose oxidase,
acetylcholinesterase,
enterokinase,
tyrosinase, and
xanthine oxidase.

Preferred enzymes are β-D-galactosidase, glucose oxidase, horseradish peroxidase, and alkaline phosphatase. Most preferred is β-D-galactosidase.

β-D-Galactosidase is an enzyme purified from the bacterium E. coli and is commercially available. This enzyme has several desirable characteristics:

(a) it has a very high enzymic turnover number;
(b) it possesses a simple colorimetric substrate;
(c) it is a relatively stable enzyme;
(d) it lacks interferences from most biological specimens; and most importantly,
(e) it possesses multiple (12-20) free sulfhydryl groups about the surface of the enzyme which are not required for enzymatic activity.

Macromolecular complexes of covalently linked enzyme can be synthesized by crosslinking the enzyme via selected functional groups using a selected crosslinking reagent. Suitable crosslinking reagents are homobifunctional reagents and heterobifunctional reagents such as those listed below.

If the enzyme to be polymerized is β-D-galactosidase, the thiol-specific homobifunctional reagent O-phenylenedimaleimide is preferred.

CROSSLINKING REAGENTS

Heterobifunctional m-maleimidobenzoyl N-hydroxysuccinimide ester
N-succinimidyl 3-(2-pyridyldithio)propionate
succinimidyl 4-(N-maleimidomethyl)cyclohexane-1-carboxylate
succinimidyl-4-(p-maleimidophenyl)butyrate
N-succinimidyl (4-iodoacetyl)aminobenzoate
maleimidohexanoyl-N-hydroxysuccinimide ester
m-maleimidobenzoyl sulfosuccinimide ester
sulfosuccinimidyl 4-(N-maleimidomethyl)cyclohexane-1-carboxylate
sulfosuccinimidyl 4-(p-maleimidophenyl)butyrate
N-5-azido-2-nitrobenzoyloxysuccinimide
N-hydroxysuccinimidyl-4-azidobenzoate
sulfosuccinimidyl 6-(4'-azido-2'-nitrophenylamino)hexanoate

Homobifunctional o-phenylenedimaleimide
3,3'-dithiobis(sulfosuccinimidyl propionate)
bis(sulfosuccinimidyl)suberate
bis(maleimido)methyl ester
dimethyl suberimidate.2HCl
dimethyl pimelimidate
dimethyl adipimidate
dithiobis(succinimidyl propionate)

The polymerization procedure is carried out under conditions which allow for controlled and reproducible formation of a polymer of preselected size. The concentration of the enzyme, the pH of the buffer, the stoichiometry of free functional groups relative to crosslinking reagent, the temperature, and the time of reaction are all important factors in achieving this controllable process.

For example, at high protein concentrations, the polymerization occurs so rapidly and to such a large extent that the polymeric enzyme gelatinizes and falls out of solution. On the other hand, if the enzyme concentration is too low, very little polymerization occurs. The pH of the reaction is an important factor in regard to the stability of the crosslinking reagent in aqueous solutions and the relative pH-sensitivity of the enzyme. Generally, these crosslinking reagents are only sparingly soluble in water and also hydrolyze rapidly in aqueous solutions at pH above 6.0. The pH of the reaction, therefore, must be carefully chosen to balance the instability of the crosslinking reagent and the sensitivity of the enzyme to non-neutral pH. The temperature and time of the reaction are also important, again because of the instability of the crosslinking reagents and the potential inactivation of the enzymes when exposed to less than optimal pH. Finally, the stoichiometry of the crosslinking reagent and the functional groups on the enzyme to be crosslinked is important in achieving the preferred degree of polymerization. This optimal stoichiometry must be determined experimentally and most likely will be slightly different for each enzyme and/or crosslinking reagent.

After optimal crosslinking has been achieved, the reaction can be stopped by the addition of an appropriate quenching reagent which consumes the excess crosslinking reagent or functional groups on the enzyme. The polymerized enzyme can be separated from the reaction mixture by gel filtration chromatography to obtain a pure polymerized, homogeneous, macromolecular species of known size.

Antibody, preferably Fab'—SH fragment, is then coupled to the "outside of the polymeric enzyme via excess functional groups provided by the crosslinking reagent used to stop the polymerization reaction or the introduction of a second site-specific crosslinking reagent. The stoichiometry of the antibody-enzyme conjugate can be chosen carefully to obtain maximal sensitivity and minimal background activity in an immunoassay. This optimization must be performed experimentally by coupling antibodies (or antibody-fragments) to polymeric enzyme at various molar ratios and then testing the resulting conjugates in the immunoassay of choice. In general, it is desirable to use monospecific antibodies for the analyte in question. Procedures for the preparation of monspecific antibody reagents by affinity purification are well known in the art [Weir, D. M., Handbook of Experimental Immunology, Blackwell Sci. Publ., London, 3rd ed., 1978]. The antibody can be of polyclonal or monoclonal origin. Monovalent antibody fragments, i.e., those having only one antigenic binding site, can be prepared from the affinity purified antibodies by procedures also well known in the art.

For example, Fab-fragments are obtained by papain digestion of IgG; Fab'-fragments are obtained by disulfide reduction of F(ab')$_2$ fragments obtained by pepsin digestion of IgG. Half-antibodies are obtained by selective sulfitolysis of IgG. These procedures are described in "Handbook of Experimental Immunology", Weir, D. M., cited above.

The utilization of antibody-fragments which possess free sulhydryls at the hinge region (e.g., Fab'—SH or half-IgG) are preferred because the polymeric enzyme complexes can be coupled through these thiols using sulfhydryl specific crosslinking reagents [e.g., o-phenylenedimaleimide or succinimidyl 4-(N-maleimidomethyl)cyclohexane-1-carboxylate]—thus keeping the chemistry and coupling far removed from the antibody binding sites. The same argument holds true for the coupling of polymeric enzymes through the carbohydrate moiety of the antibody molecule. Although the former are preferred, coupling can be achieved through the amino groups or carboxyl groups of the antibody using appropriate site-specific crosslinking reagents.

The use of these polymeric enzyme-antibody conjugates in double antibody or single antibody immunometric assays provides enhanced signal generation and, therefore, shorter assay times and higher overall sensitivity. Furthermore, the manner in which these antibody-enzyme conjugates are prepared provides for maximum maintenance of enzymatic and immunoreactivity and minimal nonspecific adsorption.

The invention is illustrated by the following nonlimiting examples.

EXAMPLE 1

Polymerization of β-D-Galactosidase and Coupling to Fab'-SH

β-D-Galactosidase (lyophilyzed) was dissolved in 0.05M Tris—Cl, 0.15M NaCl, 0.0001M MgCl$_2$, 0.002M EDTA, pH 6.5, at various concentrations (1–4 mg/mL protein) and then treated with a five-fold molar excess of o-phenylenedimaleimide (dissolved at 1 mg/mL in N,N'-dimethylformamide). After a 16 hour reaction period at 4° C., an additional aliquot (200-fold molar excess) of o-phenylenedimaleimide was added. After a 45 minute incubation at 23° C., the enzyme mixtures were applied to Sephadex G-25 columns (1.5×40 cm) equilibrated with the same Tris—NaCl—MgCl$_2$ buffer (no EDTA).

Table 1, below, illustrates how the concentration of β-D-galactosidase used in the polymerization step influences the ultimate size of polymeric-enzyme conjugate and its specific enzymic activity.

TABLE 1

| β-D-galactosidase (mg/mL) | Molecular Weight of Polymeric Enzyme* | Specific Activity (μmols of o-nitrophenolate ion/min/mg polymeric enzyme) |
| --- | --- | --- |
| monomer | 540,000 | 639 |
| 1.0 | 3,400,000 | 530 |
| 2.0 | 18,000,000 | 529 |
| 3.0 | 39–66,000,000 | 603 |
| 4.0 | 714–870,000,000 | 562 |

*Determined by elution position on Sephacryl S-1000 column.

The β-D-galactosidase polymers which eluted from the columns in the void volumes were combined with various amounts of freshly reduced affinity purified Fab'—SH fragments.

The Fab'—SH fragments were prepared from digoxin specific IgG which itself was immunopurified from rabbit antiserum to digoxin-bovine serum albumin in a one step affinity chromatography on a ouabain-agarose column. The details of this procedure are described further by Freytag et al., [Clin. Chem., Volume 84, 417 (1984)]. The digoxin-specific IgG was >95% pure as determined by sodium dodecyl sulfate polyacrylamide gel electrophoresis and had an affinity constant of $1\times10^9 M^{-1}$. The IgG was converted into F(ab')$_2$ fragments using pepsin digestion, also as described previously. [Freytag et al., cited above.]

The conjugation of Fab'—SH to the various maleimido-β-galactosidase polymers was allowed to proceed at 4° C. for 16 hours, after which the various conjugates were subjected to column chromatography on Sephacryl S-1000 (Pharmacia Fine Chemicals, Uppsala, Sweden). The peak elution positions of the conjugates allowed for the determination of the molecular sizes of the antibody-enzyme conjugates.

Affinity Column-Mediated Immunometric Assay

The performance of the various Fab'-polymeric β-galactosidase conjugates was analyzed in an affinity column-mediated immunometric assay for digoxin. This assay was performed by first mixing aliquots of the various Fab'-β-galactosidase conjugates (1–10 μL) with serum calibrators (100 μL) containing various amounts of digoxin (0, 0.5, 1.5, 3.5, & 5.0 ng/mL). After a 10–15 minute preincubation period at room temperature, the reaction mixtures were eluted through ouabain-bovine serum albumin affinity columns (0.5×8 cm) at a flow rate of 1 mL/min. The amount of β-galactosidase activity which eluted from the column was quantified spectrophotometrically at 37° C. using 2.5 mM o-nitrophenylgalactopyranoside dissolved in 0.05M Tris—Cl, pH 7.5, 0.15M NaCl, 0.001M MgCl$_2$. The change in absorbance due to enzymatically generated o-nitrophenolate ion was measured at 405 nm.

Table 2 illustrates how both the molecular size of the antibody-enzyme conjugate and the molar ratio of Fab'-fragments to β-D-galactosidase affect the overall assay performance in terms of background and assay sensitivity.

TABLE 2

| Molec. Wgt. of Polymeric β-gal | Fab'/Polymeric- β-Gal Molar Ratio | (Abs/min) Background | (Abs/min per ng/mL digoxin) Sensitivity |
|---|---|---|---|
| 540,000 | 1/1 | 0.020 | 0.010 |
| 13,000,000 | 47/1 | 0.044 | 0.025 |
| 13,000,000 | 24/1 | 0.145 | 0.068 |
| 20,000,000 | 30/1 | 0.101 | 0.035 |
| 20,000,000 | 20/1 | 0.223 | 0.066 |
| 35,000,000 | 40/1 | 0.075 | 0.108 |
| 714,000,000 | 793/1 | 0.378 | 0.308 |

As can be seen from the above data, the general trend is that the larger the molecular weight of the polymeric β-galactosidase, the greater the maximum sensitivity that is achievable with this assay. Also, for any polymeric β-galactosidase of a given molecular weight, the greater the number of antibody sites bound per polymeric β-galactosidase, the lower the background blank activity as well as the sensitivity.

A direct comparison of the enhancement in sensitivity achievable with an optimized prepolymerized enzyme (molecular weight of 20,000,000 and an Fab' to β-galactosidase molar ratio of 20) versus a monomeric enzyme conjugate is shown in FIG. 1. Although the use of monomeric conjugate does provide a linear calibration curve, the use of prepolymerized Fab'-β-galactosidase conjugate provides 20 to 30 times more sensitivity.

Column-Mediated Double Antibody Immunometric Assay

The performance of an Fab'-polymeric β-galactosidase conjugate (Molecular Weight=35,000,000; Fab'-/β—Gal=40/1) was compared to that of an Fab' monomeric-β-galactosidase conjugate in a sandwich-type double antibody immunometric assay. The analyte, digoxin, was made polyepitopic (i.e., possessing multiply occurring antigenic determinants) by covalently coupling 7-12 digoxin molecules to bovine serum albumin using the following procedure: Crystalline digoxin (1.25 g) was dissolved in 75 mL of ethanol and then combined with 150 mL of water containing 1.83 g of sodium metaperiodate (NaIO$_4$). After two hours at room temperature (20°-23° C.) with stirring (in the dark), oxidation was stopped by passage of the mixture through a 100 mL bed of Dowex 1-X8 anion exchange resin (Bio-Rad Laboratories, Richmond, CA 94804). The eluate was combined with a solution of bovine serum albumin (2.5 g dissolved in 100 mL of 0.3M sodium phosphate buffer, pH 8.5). After one hour at 20°-23° C., 0.24 g of solid sodium cyanoborohydride was added with mixing, and the solution was allowed to react for 48 hours at 20°-23° C. Unconjugated digoxin and reaction by-products were removed from the solution by dialysis (visking membrane, 6000-8000 molecular weight cutoff) against running distilled water for two days and then against 20 volumes of 0.015M sodium phosphate buffer, pH 7.0, 0.15M NaCl at 4° C.

An immobilized anti-digoxin support was synthesized. Twenty-six milligrams of affinity purified anti-digoxin IgG dissolved in 20 mL of 0.1M sodium borate, pH 8.5, was combined with 5 g of carbodiimidazole-activated controlled pore glass beads [Carbodiimidazole-activated glycerol coated controlled pore glass beads of 250 Å pore size, 120/200 mesh, from Pierce Chemical Co., Rockford, IL 61105]. After 16 hours of reaction time at 4° C. with constant gentle mixing, the glass beads were washed with 20 mL of 0.1M sodium borate, pH 8.5, and then recombined with 20 mL of 0.1M sodium phosphate buffer, pH 7.0, containing 1 mg/mL human serum albumin. After another overnight reaction period at 4° C., the glass beads were washed extensively with 0.015M sodium phosphate, pH 7.0, 0.15M NaCl (500 mL). The resin was packed into small columns (5×80 mm) for use.

Assay response curves were generated by first mixing 200 μL aliquots of samples containing various amounts of digoxin-BSA with approximately 100 fmols of antibody-enzyme conjugate (either monomeric or polymeric Fab'-β-galactosidase, prepared as described above). After a 60 minute incubation period at ambient temperature (20°-23° C.), the sample mixture was eluted through an anti-digoxin-controlled pore glass column at a flow rate of 10 μL/s followed by 1.5 mL of 0.15M sodium phosphate buffer, pH 7.8. The amount of β-galactosidase activity which eluted through the column in the unbound fraction was quantitated by adding 2.3 mL of water containing 3 mg of o-nitrophenylgalactopyranoside. The production of yellow color (o-nitrophenolate ion) was measured spectrophotometrically at 405 nm. The data are shown in Table 3. Although the two conjugates performed similarly in terms of immunochemical sensitivity, the polymeric-enzyme conjugate provided much more signal production. Thus, the time to measure a result was considerably less using the polymeric-enzyme conjugate. For example, between zero and $1.2 \times 10^{-18}$ mols of digoxin-BSA, there was a change in absorbance at 405 nm per minute of 0.015 using the polymeric-enzyme conjugate, whereas the change in absorbance was only 0.002 using the monomeric-enzyme conjugate.

TABLE 3

| mols of Digoxin-BSA per sample | ΔAbs 405 nm per min. | |
|---|---|---|
| | polymeric-enzyme conjugate | monomeric-enzyme conjugate |
| 0 | .170 | .018 |
| $1.2 \times 10^{-20}$ | .164 | — |
| $1.2 \times 10^{-18}$ | .156 | .016 |
| $1.2 \times 10^{-16}$ | .142 | .013 |
| $1.2 \times 10^{-14}$ | .124 | .008 |
| $1.2 \times 10^{-12}$ | .057 | .004 |

EXAMPLE 2

Polymerization of β-Galactosidase and Coupling to IgG

Polymerization of β-Galactosidase

Six milligrams of β-galactosidase (enzyme immunoassay grade, Boehringer-Mannheim Corp., Indianapolis, IN) was dissolved in 3 mL of 0.05M Tris—HCl, pH 7.0, 0.15M NaCl, 1 mM MgCl$_2$, 5 mM EDTA and then mixed with 14.7 μg of o-phenylenedimaleimide dissolved in 1.1 μL of N,N'-dimethylformamide. After 16 hours at 4° C., the mixture was chromatographed on a Sephadex G-25 column (1.5×40 cm) using the same Tris—NaCl—MgCl$_2$— EDTA buffer described above. The polymerized β-galactosidase was pooled from the void volume fractions.

One milliliter (0.89 mg) of monoclonal IgG to β-human chorionicgonadotropin (β-hCG) [Hybritech Corporation, San Diego, CA] was dialyzed against 1 liter of 0.015M sodium phosphate, pH 7.0, 0.15M NaCl, 1 mM EDTA at 4° C. for 16 hours. After dialysis, the antibody was reacted with 59 μg of succinimidyl-4-(N- maleimidomethyl)cyclohexane-1-carboxylate dissolved in 5.9 μL of N,N'-dimethylformamide for 1 hour at 20°–23° C. The reaction was terminated by passing the mixture on a Sephadex G-25 column (1.5×40 cm) equilibrated in 0.015M sodium phosphate, pH 7.0, 0.15M NaCl, 1 mM EDTA. A maleimido-IgG adduct eluting in the void volume of the column was pooled and concentrated to 1.13 mL by pressure filtration.

The conjugation of antibody to polymeric enzyme was performed by combining 1.13 mL (0.61 mg/mL) of the maleimido-IgG with 5.73 mL of the polymerized β-galactosidase (0.87 mg/mL) and mixing for 20 hours at 4° C. The mixture was concentrated to 2.0 mL by pressure filtration and then chromatographed on a Sepharose 4B column (1.5×90 cm) equilibrated with 0.05M Tris—HCl, pH 7.5, 0.15M NaCl, 0.001M MgCl$_2$, at 4° C. The IgG-β-galactosidase conjugate which eluted in the void volume of the column was pooled and stored at 4° C.

Preparation of β-hCG Affinity Column

Ten milligrams of β-hCG (Diosynth. Chicago, IL) was dissolved in 5 mL of 0.1M sodium borate buffer, pH 8.5, and combined with 5 g of carbodiimidazole-activated controlled pore glass beads (CDI-CPG, Pierce Chemical Co., Rockford, IL) and mixed for 16 hours at 4° C. Ten milliliters of a 10 mg/mL solution of bovine serum albumin dissolved in 0.1M sodium borate buffer was added to the resin, and mixing was continued for another 16 hours at 4° C. The affinity resin was then washed extensively with 0.15M sodium phosphate buffer, pH 7.8.

Affinity Column Mediated Immunometric Assay for β-hCG

Figure 2:
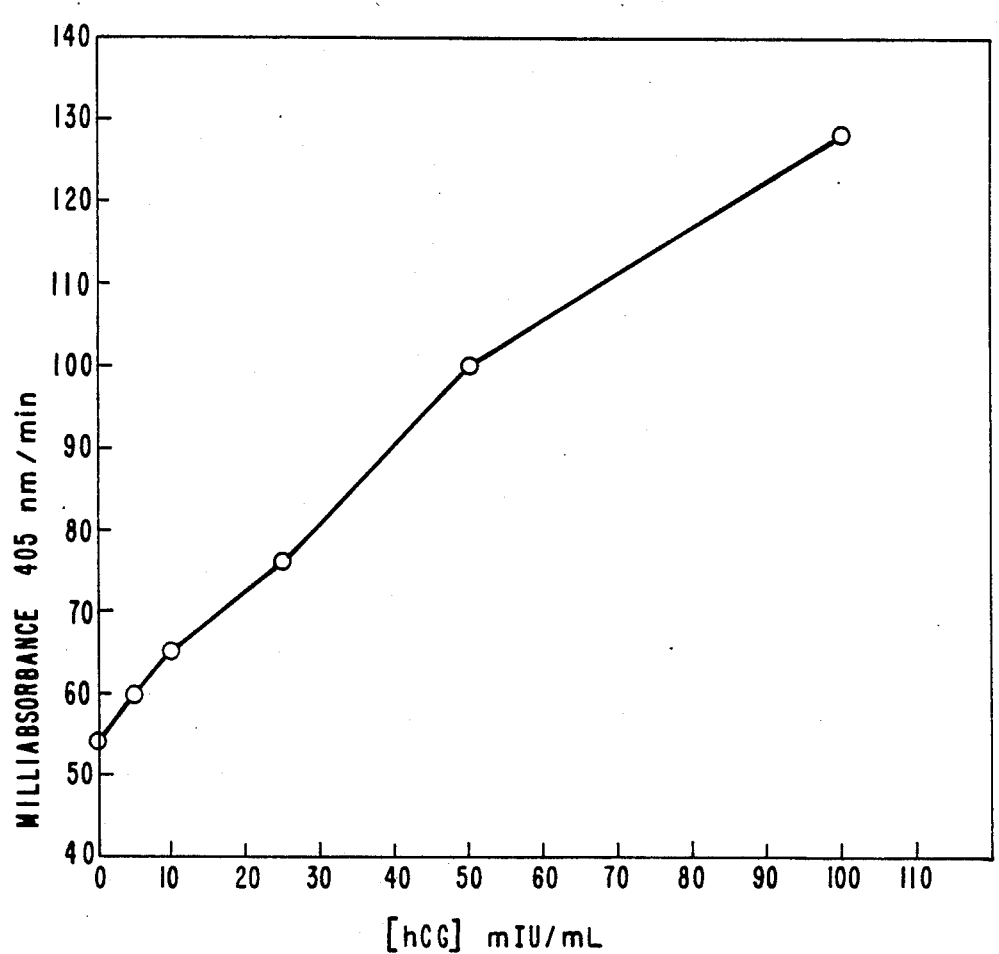

One hundred microliters of β-hCG calibrators (0, 5, 10, 25, 50 & 100 mIU/mL) were mixed with 5 μL of the IgG-β-galactosidase conjugate for 60 minutes at 20° C. The samples were then eluted consecutively through a reusable β-hCG affinity column (3×15 mm) at 5 μL/sec followed by 250 μL of 0.15M sodium phosphate buffer, pH 7.8. An aliquot (77 μL) of the column effluent was assayed by combining it with 320 μL of 2.5 mM o-nitrophenylgalactoside at 37° C. The production of yellow color (405 nm) was quantified spectrophotometrically in a kinetic rate mode. The results of this dose response curve are shown in FIG. 2. The results presented in this figure represent state-of-the-art sensitivity and speed for the detection of β-hCG.

EXAMPLE 3

Polymerization of Glucose Oxidase and Coupling to IgG or F(ab')$_2$

Glucose oxidase dissolved in sodium phosphate buffer, pH 6.5, 1–4 mg/mL protein, is reacted with a 25–200 fold molar excess of S-acetylmercaptosuccinic anhydride dissolved in N,N'-dimethylformamide. After a reaction period of 30–60 minutes at 20°–23° C. or overnight at 4° C., an aliquot of 0.05M hydroxylamine—HCl, pH 7.0, 1 mM EDTA is added for five minutes at 30° C., and then the sulfhydryl-activated enzyme is desalted on a small (1.5×40 cm) Sephadex G-25 column. The sulfhydryl-activated enzyme is collected in the void volume fractions.

An additional sample of glucose oxidase (1–5 mg/mL protein) dissolved in sodium phosphate buffer, pH 6.5, is reacted with 10–100 fold molar excess of succinimidyl 4-(N-maleimidomethyl)cyclohexane-1-carboxylate (SMCC) for 30–90 minutes at 20°–23° C. The sample is then desalted on a small (1.5×40 cm) Sephadex G-25 column. The maleimido-activated enzyme is collected in the void volume fractions.

The sulfhydryl-activated glucose oxidase and the maleimido-activated glucose oxidase are combined at various molar ratios (e.g. 1:1, 2:1, or 1:2) for 4–16 hours at 4° C. The coupling reaction is then quenched by the addition of 2-mercaptoethylamine (slight molar excess over maleimido content) and the polymeric enzyme is desalted on a Sephadex G-25 column.

IgG or F(ab')$_2$ fragments (1–5 mg/mL protein) dissolved in sodium phosphate buffer, pH 6.5, are reacted with a 20–30 fold molar excess of SMCC for 30–90 minutes at 20°–23° C. and then desalted on a Sephadex G-25 column. The maleimido-activated antibody is combined with the prepolymerized glucose oxidase at various enzyme to antibody ratios (e.g., 1:1, 1:2 or 2:1) and allowed to react at 4° C. for 16–20 hours. The conjugate is then chromatographed on a Sepharose 4B column equilibrated in 0.1M sodium phosphate buffer, pH 7.0, and the conjugate is collected in the void volume fractions. Use of this prepolymerized glucose oxidase-antibody conjugate in a single or double immunometric assay is expected to provide enhanced signal generation over that produced by a conjugate of antibody and monomeric glucose oxidase.

We claim:

1. A method for producing a polymeric-enzyme/antibody conjugate, comprising:
    (1) covalently coupling at least two enzyme molecules to produce a prepolymerized enzyme; and
    (2) coupling covalently the prepolymerized enzyme to an antibody or fragment thereof.

2. The method of claim 1 wherein the enzyme is selected from the group consisting of
    β-D-galactosidase, glucose oxidase, horseradish peroxidase, alkaline phosphatase, β-lactamase, glucose-6-phosphate dehydrogenase, urease, uricase, superoxide dismutase, luciferase, pyruvate kinase, lactate dehydrogenase, galactose oxidase, acetylcholinesterase, enterokinase, tyrosinase, and xanthine oxidase.

3. The method of claim 2 wherein the enzyme is selected from the group consisting of β-D-galactosidase, glucose oxidase, horseradish peroxidase and alkaline phosphatase.

4. The method of claim 3 wherein the enzyme is β-D-galactosidase.

5. The method of claim 1 wherein the coupling step (1) is carried out using a crosslinking reagent.

6. The method of claim 5 wherein the reagent is a homobifunctional crosslinking reagent.

7. The method of claim 6 wherein the homobifunctional crosslinking reagent is selected from the group consisting of o-phenylenedimaleimide, 3,3'-dithiobis(sulfosuccinimidyl propionate), bis(sulfosuccinimidyl)suberate, bis(maleimido) methyl ester, dimethyl suberimidate.2HCl, dimethyl pimilimidate, dimethyl adipimidate, and dithiobis(succinimidyl propionate).

8. The method of claim 5 wherein the crosslinking reagent is a heterobifunctional crosslinking reagent selected from the group consisting of m-maleimidobenzoyl N-hydroxysuccinimide ester, N-succinimidyl 3-(2-pyridyldithio)propionate, succinimidyl 4-(N-maleimidomethyl)cyclohexane-1-carboxylate, succinimidyl-4-(p-maleimidophenyl)butyrate, N-succinimidyl (4-iodoacetyl)aminobenzoate, maleimidohexanoyl-N-hydroxysuccinimide ester, m-maleimidobenzoyl sulfosuccinimide ester, sulfosuccinimidyl 4-(N-maleimidomethyl)cyclohexane-1-carboxylate, sulfosuccinimidyl 4-(p-maleimidophenyl)butyrate, N-5-azido-2-nitrobenzoyloxysuccinimide, N-hydroxysuccinimidyl-4-azidobenzoate, and sulfosuccinimidyl 6-(4'-azido-2'-nitrophenylamino)hexanoate.

9. The method of claim 7 wherein the crosslinking reagent is o-phenylenedimaleimide.

10. The method of claim 1 wherein the coupling step (2) is carried out using a crosslinking reagent.

11. The method of claim 10 wherein the crosslinking reagent is a homobifunctional crosslinking reagent selected from the group consisting of o-phenylenedimaleimide, 3,3'-dithiobis(sulfosuccinimidyl proprionate), bis(sulfosuccinimidyl)suberate, bis(maleimido)methyl ester, dimethyl suberimidate•2HCl, dimethyl pimelimidate, dimethyl adipimidate, and dithiobis(succinimidyl propionate).

12. The method of claim 10 wherein the crosslinking reagent is a heterobifunctional crosslinking reagent selected from the group consisting of m-maleimidobenzoyl N-hydroxysuccinimide ester, N-succinimidyl 3-(2-pyridyldithio)propionate, succinimidyl 4-(N-maleimidomethyl)cyclohexane-1-carboxylate, succinimidyl-4-(p-maleimidophenyl)butyrate, N-succinimidyl (4-iodoacetyl)aminobenzoate, maleimidohexanoyl-N-hydroxysuccinimide ester, m-maleimidobenzoyl sulfosuccinimide ester, sulfosuccinimidyl 4-(N-maleimidomethyl)cyclohexane-1-carboxylate, sulfosuccinimidyl 4-(p-maleimidophenyl)butyrate, N-5-azido-2-nitrobenzoyloxysuccinimide, N-hydroxysuccinimidyl-4-azidobenzoate, and sulfosuccinimidyl 6-(4'-azido-2'-nitrophenylamino)hexanoate.

13. The method of claim 1 wherein the antibody or fragment thereof is an IgG molecule, Fab fragment, Fab' fragment, F(ab')$_2$ fragment, or half-antibody.

14. The method of claim 13 wherein the Fab' fragment is an Fab'—SH fragment.

15. The method of claim 1 wherein the antibody is an Fab'—SH fragment, the enzyme is β-D-galactosidase, and the coupling steps (1) and (2) are carried out using o-phenylenedimaleimide.

16. In an immunoassay for the determination of an analyte in a liquid sample, said immunoassay comprising:
  (1) contacting the sample with an enzyme-labeled anti-analyte antibody to form (i) a complex comprising enzyme-labeled anti-analyte antibody and analyte and (ii) free enzyme-labeled anti-analyte antibody;
  (2) separating the complex from the free enzyme-labeled anti-analyte antibody;
  (3) measuring the enzymatic activity of either the complex or the free enzyme-labeled anti-analyte antibody; and
  (4) relating the enzymatic activity to the amount of analyte initially present in the sample,
the improvement comprising:
  using as the enzyme-labeled anti-analyte antibody, a covalent conjugate of a prepolymerized enzyme and an antibody or fragment thereof.

17. The method of claim 16 wherein the analyte is digoxin and the covalent conjugate comprises an Fab' fragment and prepolymerized β-D-galactosidase of molecular weight from about 20,000,000 to about 35,000,000, the Fab' fragment and prepolymerized β-D-galactosidase at a molar ratio of from about 20:1 to about 40:1, respectively.

18. A conjugate comprising a prepolymerized enzyme comprising at least two enzyme molecules covalently coupled, said prepolymerized enzyme covalently coupled to an antibody or fragment thereof.

19. The conjugate of claim 18 wherein the enzyme is selected from the group consisting of β-D-galactosidase, glucose oxidase, horseradish peroxidase, alkaline phosphatase, β-lactamase, glucose-6-phosphate dehydrogenase, urease, uricase, superoxide dismutase, luciferase, pyruvate kinase, lactate dehydrogenase, galactose oxidase, acetylcholinesterase, enterokinase, tyrosinase, and xanthine oxidase.

20. The conjugate of claim 19 wherein the enzyme is selected from the group consisting of β-D-galactosidase, glucose oxidase, horseradish peroxidase and alkaline phosphatase.

21. The conjugate of claim 20 wherein the enzyme is β-D-galactosidase.

22. The conjugate of claim 21 wherein the antibody or fragment thereof is an Fab' fragment.

* * * * *